United States Patent
Heiliger et al.

(10) Patent No.: US 6,761,832 B1
(45) Date of Patent: Jul. 13, 2004

(54) PROCESS FOR THE PRODUCTION OF DITHIOPHOSPHORIC ACID POLYSULFIDE MIXTURES

(75) Inventors: Ludger Heiliger, Neustadt (DE); Alfred Pauli, Reilingen (DE); Joachim Hegmann, Limburgerhof (DE); Clemens Schudok, Bobenheim-Roxheim (DE); Thomas Früh, Ludwigshafen (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 0 days.

(21) Appl. No.: 09/499,363

(22) Filed: Feb. 10, 2000

(30) Foreign Application Priority Data

Feb. 19, 1999 (DE) .......................................... 199 06 986

(51) Int. Cl.⁷ ..................... C07C 319/24; C07C 323/00; C08K 5/37; C08K 5/372; C08K 5/49
(52) U.S. Cl. ............................ 252/182.17; 252/182.14; 252/182.18; 252/182.3; 558/71; 558/112; 558/123; 558/129; 558/151
(58) Field of Search ...................... 252/182.17, 182.14, 252/182.18, 182.3; 558/71, 112, 123, 129, 151

(56) References Cited

U.S. PATENT DOCUMENTS

| | | | | |
|---|---|---|---|---|
| 2,237,627 A | * | 4/1941 | Olin | 568/21 |
| 3,642,727 A | * | 2/1972 | Ashworth et al. | 525/341 |
| 3,979,369 A | * | 9/1976 | Trivette, Jr. | 525/332.7 |
| 5,028,729 A | * | 7/1991 | Schubart et al. | 558/129 |
| 5,151,510 A | * | 9/1992 | Stec et al. | 536/25.3 |
| 5,403,501 A | * | 4/1995 | Schwind | 508/186 |
| 5,565,599 A | * | 10/1996 | Graf et al. | 558/71 |
| 6,186,204 B1 | * | 2/2001 | Sasaka et al. | 152/450 |

FOREIGN PATENT DOCUMENTS

| | | |
|---|---|---|
| DE | 228722 | 10/1985 |
| GB | 1 401 435 | * 7/1975 |

OTHER PUBLICATIONS

Journal Of Applied Polymer Science, Vol 19, pp 865–877 (1975) article entitled: "Bis(DiIsopropyl) thiophosphoyl disulfide in cis 1,4–Polyisoprene vulcanization Reactions As Sulfur Donor", by Pimblott et al.*

Derwent–Acc–No 1986–048663 which is the English Language Abstract of DD 228722A, (1986).*

* cited by examiner

*Primary Examiner*—Joseph D. Anthony
(74) *Attorney, Agent, or Firm*—Joseph C. Gil; Noland J. Cheung; Jennifer R. Seng

(57) ABSTRACT

This invention relates to a process for the production of dithiophosphoric acid poly-sulfide mixtures, which is characterized in that dithiophosphoric acid disulfides are reacted with sulfur at elevated temperatures. The dithiophosphoric acid polysulfide mixtures produced using the process according to the present invention are used as sulfur donors for the vulcanization of natural and synthetic rubbers and in the latex vulcanization of natural and synthetic rubber latex.

1 Claim, No Drawings

PROCESS FOR THE PRODUCTION OF DITHIOPHOSPHORIC ACID POLYSULFIDE MIXTURES

FIELD OF THE INVENTION

This invention relates to a novel process for the production of dithiophosphoric acid polysulfide mixtures starting from dithiophosphoric acid disulfide.

BACKGROUND OF THE INVENTION

Dithiophosphoric acid polysulfides are known, as is the use thereof as vulcanizing agents or vulcanizing accelerators for the vulcanization of rubber (c.f. DE 19 36 694, DE 22 49 090 and DE 44 31 727). Dithiophosphoric acid polysulfides may be produced from the corresponding dithiophosphoric acids or the alkali metal salts thereof and sulfur chlorides, such as disulfur dichloride or sulfur dichloride.

The disadvantages of reacting dithiophosphoric acids with sulfur chlorides include the elevated corrosiveness of the sulfur chlorides and the unpleasant odor thereof, which gives rise to handling problems and entails appropriate, complex plant and equipment. According to EP 0 383 102 A1, sulfur dichloride, moreover, very readily disproportionates, such that dithiophosphoric acid trisulfides are not directly obtainable using this process.

Additionally, the dithiophosphoric acid tetrasulfides obtained using the process described above have a tendency, due to the low stability thereof, to eliminate sulfur. In order to prevent this, it is necessary to stabilize the dithiophosphoric acid tetrachlorides against sulfur precipitation as is described, for example, in DE 44 31 727.

SUMMARY OF THE INVENTION

The object of the present invention is accordingly to provide a process for the production of dithiophosphoric acid polysulfide mixtures which avoids the use of sulfur chlorides and gives rise to sulfur-stable dithiophosphoric acid polysulfide mixtures.

DETAILED DESCRIPTION OF THE INVENTION

The present invention accordingly provides a process for the production of dithiophosphoric acid polysulfide mixtures of the formula

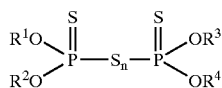

in which
R$^1$ to R$^4$ are identical or different and denote a linear or branched C$_1$–C$_{18}$ alkyl residue, C$_1$–C$_{18}$ alkenyl residue, C$_5$–C$_{28}$ cycloalkyl residue, C$_5$–C$_{28}$ cycloalkenyl residue as well as a C$_6$–C$_{28}$ aryl residues or C$_7$–C$_{28}$ aralkyl residue and
n denotes a number from 2.5 to 3.5,
which is characterized in that dithiophosphoric acid disulfides of the formula

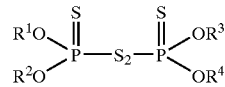

in which
R$^1$ to R$^4$ have the above-stated meaning,
are reacted with 0.5 to 1.5. mol of sulfur, optionally in the presence of a solvent, at temperatures of 100 to 140° C.

The numeric values for n are determined statistically in accordance with the sulfur chain distribution in the molecule.

The residues R$^1$ to R$^4$ of the above-stated formulae may be substituted by suitable residues which are not disruptive to the subsequent use of the polysulfides, wherein alkyl residues and cycloalkyl residues may, in particular, be mentioned.

Preferred residues R$^1$ to R$^4$ are C$_6$–C$_{12}$ alkyl residues, in particular C$_8$–C$_{12}$ alkyl residues, in particular branched alkyl residues, such as 2-ethylhexyl.

The dithiophosphoric acid polysulfide mixtures produced according to the invention are preferably those in which n denotes numbers from 2.8 to 3.3.

The dithiophosphoric acid disulfides to be used in the process according to the invention are also known and are described, for example, in the *Journal of Applied Polymer Science*, volume 19, pp. 865–877 (1975). The disulfides are produced, for example, by oxidizing dithiophosphoric acid with hydrogen peroxide or HOCl or a mixture of potassium bromide and hydrogen peroxide.

In the process according to the present invention, the disulfides used are preferably reacted with 0.8 to 1.3 mol of elemental sulfur, wherein temperatures of 110 to 130° C., in particular of 120 to 130° C., are preferred.

If the reaction is to be performed in solution, the solvents used are in particular aliphatic solvents, for example naphtha, aromatic solvents, for example toluene, or halogenated aromatic solvents, such as chlorobenzene. The solvents may, of course, also be used as a mixture with each other.

The quantity of solvent may readily be determined by appropriate preliminary testing. Conventional quantities of solvent are from 0.1 to 50 wt %, relative to the weight of the disulfide used.

It is furthermore possible to add hydrogen peroxide to the reaction according to the invention in order to prevent any possible color changes. In this case, the hydrogen peroxide is used in quantities of 0.1% to 5 wt %, relative to the weight of the disulfide used.

Depending upon the reaction conditions employed, the reaction time ranges from approx. 10 minutes to approx. 6 hours.

Since the dithiophosphoric acid polysulfides produced according to the present invention are particularly sulfur-stable, i.e., they have no tendency to precipitate sulfur crystals, they are particularly suitable for use as sulfur donors for the vulcanization of natural and synthetic rubbers and for latex vulcanization of natural and synthetic rubber latex.

The invention is further illustrated but is not intended to be limited by the following examples in which all parts and percentages are by weight unless otherwise specified.

EXAMPLES

Example 1

999.0 g (2.6179 mol) of O,O-di-2-ethylhexyldithiophosphoric acid diester (C$_8$-DTPS) having an acid value of 147 mg. of KOH/g and 1.0 g (0.0084 mol) of potassium bromide are initially introduced at room temperature into a flask equipped with a stirrer, dropping funnel, gas inlet and reflux condenser and adjusted to a temperature of 30° C.

163.2 g (1.4399 mol) of hydrogen peroxide are then added dropwise in such a manner that the temperature in this strongly exothermic reaction does not rise above 40° C.±5° C.

In order to accelerate phase separation, 50 g of naphtha (80-110) and 10 g of sodium chloride are added and the batch left to stand at 40° C.±5° C. until the phases have cleanly separated.

The bottom aqueous phase is separated. The yellow, turbid organic phase is heated to 70° C.±5° C. and distilled under a vacuum (20 to 60 mbar). The phase is then filtered through 1% diatomaceous earth.

For the second stage of the reaction, the batch is perfused with nitrogen for 5 minutes. Then 46.1 g (1.4399 mol) of sulfur are added and the reaction mixture heated to 122° C.±2° C. in order to boil down the sulfur. The batch is stirred for 4 hours at this temperature.

The yellow product may then be packaged without filtration. Even after several months' storage, the product exhibits neither turbidity nor precipitates.

The chain distribution in the resultant dithiophosphoric acid polysulfide mixture was determined by high pressure liquid chromatography (HPLC) as is as follows:

| | | |
|---|---|---|
| n = 1  0.8% | n = 4  19.9% | n = 72.5%, in reach case relative to the area of the HPLC signals |
| n = 2  29.2% | n = 5  8.1% | |
| n = 3  35.5% | n = 6  4.4% | |

Example 2
(Comparative Example 1)

6000 g (15 mol) of O,O-di-2-ethylhexyldithiophosphoric acid diester ($C_8$-DTPS) having an acid value of 139.8 mg of KOH/g and 300 g of naphtha 80–100 are initially introduced into a vessel at room temperature. 2553.2 g of 23.5% sodium hydroxide solution (15.0 mol) are added within 1.5 h, wherein the temperature rises to 45° C. The temperature is then raised to 55° C. in order subsequently to add 1003 g (7.4 mol) of $S_2$–$Cl_2$ dropwise within 5 h. The mixture is stirred for a further 30 minutes in order to take the reaction to completion.

The batch is then adjusted to pH 7 with approx. 600 g of 8% $NaHCO_3$ solution. In order to achieve good phase separation, the temperature is raised to 65° C. and 1200 g of water are added.

Once the aqueous phase has been separated, the product is distilled for 3 h at 70° C. under a water-jet vacuum. The product is then filtered, using a filtration auxiliary, through a heated vacuum filter. The product forms yellow crystalline precipitates after only a few hours, which prove to be elemental sulfur.

Example 3
(Comparative Example 2)

6000 g (15 mol) of O,O-2-diethylhexyldithiophosphoric acid diester ($C_8$-DTPS) having an acid value of 139.8 mg of KOH/g and 300 g of naphtha 80–100 are initially introduced into a vessel at room temperature. 2553.2 g of 23.5% sodium hydroxide solution (15.0 mol) are added within 1.5 h, wherein the temperature rises to 45° C. The temperature is then raised to 55° C. in order to subsequently add 1003 g (7.4 mol) of $S_2$–$Cl_2$ dropwise within 5. The mixture is stirred for a further 30 minutes in order to take the reaction to completion.

The batch is then adjusted to pH 7 with approx. 600 g of 8% $NaHCO_3$ solution. In order to achieve good phase separation, the temperature is raised to 65° C. and 1200 g of water are added.

Once the aqueous phase has been separated, 282 g of 2-ethylhexanoic acid and 180 g of zinc oxide are added in portions at 65° C. in order to provide stabilization against sulfur precipitation. Once addition is complete, the reaction is continued for a further 2 h at 70° C.

The product is dried by distilling it for 3 h at 70° C. under a water-jet vacuum. The product is then filtered, using a filtration auxiliary, through a heated vacuum filter. The product forms yellow crystalline precipitates after only a few days, which prove to be elemental sulfur.

Although the invention has been described in detail in the foregoing for the purpose of illustration, it is to be understood that such detail is solely for that purpose and that variations can be made therein! by those skilled in the art without departing from the spirit and scope of the invention except as it may be limited by the claims.

What is claimed is:

1. A process for the production of dithiophosphoric acid polysulfide mixtures of the formula

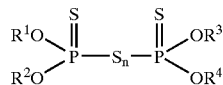

in which
R$^1$ to R$^4$ are identical or different and denote a linear or branched $C_1$–$C_{18}$ alkyl residue, $C_1$–$C_{18}$ alkenyl residue, $C_5$–$C_{28}$ cycloalkyl residue, $C_5$–$C_{28}$ cycloalkenyl residue as well as a $C_6$–$C_{28}$ aryl residue or $C_7$–$C_{28}$ aralkyl residue and
n denotes a number from 2.5 to 3.5,
comprising the step of reacting dithiophosphoric acid disulfides of the formula

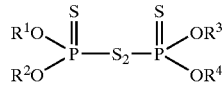

in which
R$^1$ to R$^4$ have the above-stated meaning,
with 0.5 to 1.5 mol of sulfur, optionally in the presence of a solvent, at temperatures of 100 to 140° C.

* * * * *